United States Patent
Rivera et al.

[11] Patent Number: 5,964,724
[45] Date of Patent: Oct. 12, 1999

[54] APPARATUS AND METHOD FOR BLOOD SEPARATION

[75] Inventors: John Rivera, Aurora; Son Le, Lakewood; Daniel Cheek, Highlands Ranch, all of Colo.; Richard Matt, San Jose, Calif.; Roger P. Kaminski, Parker, Colo.

[73] Assignee: Medtronic Electromedics, Inc., Parker, Colo.

[21] Appl. No.: 08/791,179

[22] Filed: Jan. 31, 1997

Related U.S. Application Data

[60] Provisional application No. 60/010,939, Jan. 31, 1996.

[51] Int. Cl.$^6$ .................................................. A61M 35/00
[52] U.S. Cl. ................................................................ 604/4
[58] Field of Search ........................... 604/4–6; 210/739, 210/745, 787; 364/413; 434/262

[56] References Cited

U.S. PATENT DOCUMENTS

| | | | |
|---|---|---|---|
| 4,804,811 | 2/1989 | Raycher et al. | 219/98 |
| 5,034,135 | 7/1991 | Fischel | 210/651 |
| 5,045,947 | 9/1991 | Beery | 358/192.1 |
| 5,068,734 | 11/1991 | Beery | 358/191.1 |
| 5,178,603 | 1/1993 | Prince | 604/6 |
| 5,298,675 | 3/1994 | Nishimoto et al. | 84/622 |
| 5,344,568 | 9/1994 | Kitaevich et al. | 604/6 |
| 5,401,238 | 3/1995 | Pirazzoli | 604/4 |
| 5,421,812 | 6/1995 | Langley et al. | 604/4 |
| 5,437,598 | 8/1995 | Antwiler | 604/6 |
| 5,505,685 | 4/1996 | Antwiler | 604/6 |
| 5,573,502 | 11/1996 | LeCocq et al. | 604/4 |
| 5,653,887 | 8/1997 | Wahl et al. | 604/6 |

*Primary Examiner*—John G. Weiss
*Assistant Examiner*—Ki Yong O
*Attorney, Agent, or Firm*—Ancel W. Lewis, Jr.

[57] ABSTRACT

The present invention is a blood separation system that is fully mechanized to collect blood from a patient, separate waste portions of the blood, wash the blood, and redirect the usable portions to a device for reinjecting the usable portions into the patient. The present invention prevents accidental activation of an improper operation that could cause harm to a patient or a shut down of the system by requiring confirmation of each step by an operator. The invention provides screen displays with detailed setup instructions, eliminating the need for secondary documentation that might not be allowed in a surgical environment. The invention also instructs the operator at the appropriate times to do certain manual steps such as opening and closing clamps. Since the opening and closing of clamps is a highly critical operation, confirmation of these steps is also required. A method and suitable apparatus is also disclosed for sequestration of platelet rich plasma whereby a blood sample is spun at a high speed sufficient to separate solid cells from the blood sample and spun at a lower speed for a predetermined time to allow platelets to elute from the solid cells.

28 Claims, 18 Drawing Sheets

```
(AUTO   /STANDARD PROGRAM          <STOP>
FILL  WASH RATE  WASH VOL   EMPTY  CENT
300       300        1000     300    5600
[FILL}     [STANDBY]      [STOP]     [MENU]
(Push Fill to begin cycle)          10:00:00
```

Fig. 4A

```
Current Run Mode:       AUTO
           [AUTO]          [MANUAL]
[ACCEPT]                          [CANCEL]
```

Fig. 4B

```
        DISPOSABLE SETUP
  7.    Remove bowl and harness assembly, insert
        bowl in centrifuge plate, lock in place.
     [MORE]      [EXIT]
```

Fig. 4C

```
        DISPOSABLE SETUP
  8.    Attach locking arms onto the bowl fill tube
        assembly and lock in place.
     [MORE]      [EXIT]
```

Fig. 4D

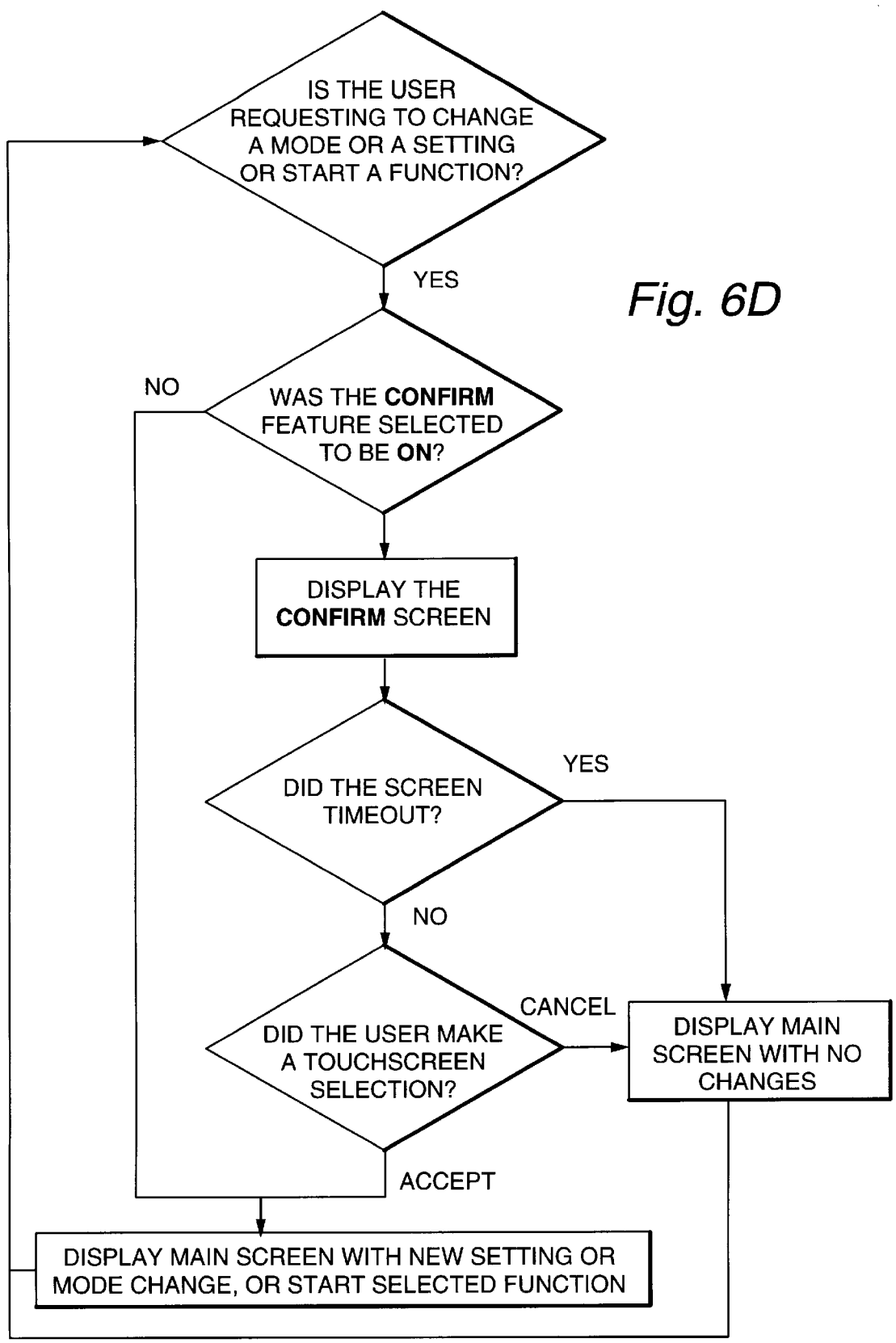

Flowchart continues at this symbol on next page

APPARATUS AND METHOD FOR BLOOD SEPARATION

This application claims the benefit under 35 U.S.C. § 119(e) of the U.S. provisional patent application No. 60/010939 filed Jan. 31, 1996.

TECHNICAL FIELD

The present invention relates to blood separation devices and methods in general and more particularly to blood separation devices and methods suitable for autotransfusion.

BACKGROUND ART

Surgical operations, including more complex operations where a substantial amount of bleeding may occur, may require transfusions during the course of the surgery to maintain a sufficient blood volume and blood pressure. Since many blood-borne diseases may exist including hepatitis, cancer and HIV, it is desirable to not require transfusion from another person. Also, if blood or blood components from the same person can be used, the necessity to match blood factors can be eliminated.

These disadvantages of receiving transfusions from donors are overcome by self-donation prior to operations. However, operations involving transfusions are not always identified in advance and few patients take the time and effort to go through the procedure. Additionally, a patient may be weakened by removal of blood prior to an operation.

Autotransfusion, whereby blood retrieved from the patient during the operation is separated so that reusable portions can be reinserted into the patient, is an effective method of overcoming the problems with transfusions. Various autotransfusion type systems currently exist but are somewhat complex to operate. For example, some autotransfusion systems require the operator to memorize a series of system steps to insure that the operator performs operations in the proper sequential order. Failure to perform the step or to perform the step in the proper sequence may cause the system to shut down or may cause morbidity in the patient.

Additionally, it is highly useful to have a blood separation system that can efficiently separate platelet and plasma from waste products in the blood. A high degree of efficiency in obtaining platelets has not been previously achieved.

It is therefore desirable to have a blood separation system that is highly efficient in extracting platelets from the blood, extracting waste products from the blood, allowing performance of operations in a simple and easy manner that does not require extensive knowledge of the system and processes, and preventing inadvertent or accidental operation of the blood separation device.

DISCLOSURE OF THE INVENTION

The present invention provides a blood separation system suitable for autotransfusion that displays instructions to guide the operator of the autotranfusion system to perform predetermined operation at predetermined times. In this manner, the operator of the system can be assured that the proper sequence of operations is being performed without a great degree of experience and knowledge of the system.

The present invention additionally requires confirmation of each operational step that is entered in the blood separation system by the operator to prevent the system from inadvertently being activated or performing an unintended operation that would necessitate the system being shut down or cause harm to the patient.

The present invention also is capable of separating blood platelets in a highly efficient manner from the blood sample by spinning the blood sample at a hard rate of approximately 5,600 rpm until the solid cells are separated from the blood sample, and then slowing the spin rate to a soft rate of about 2,400 rpm to allow the platelets to elute from the solid cells. The spin rate of 2,400 rpm is maintained for a period of approximately 60 seconds which allows the platelets to elute in a highly efficient manner.

BRIEF DESCRIPTION OF THE DRAWINGS

Details of this invention are described in connection with the accompanying drawings that bear similar reference numerals in which:

FIGS. 4A, 4B, 4C & 4D are representative views of screen displays of a blood separation system embodying the present invention.

DETAILED DESCRIPTION OF THE INVENTION

Figure 1:
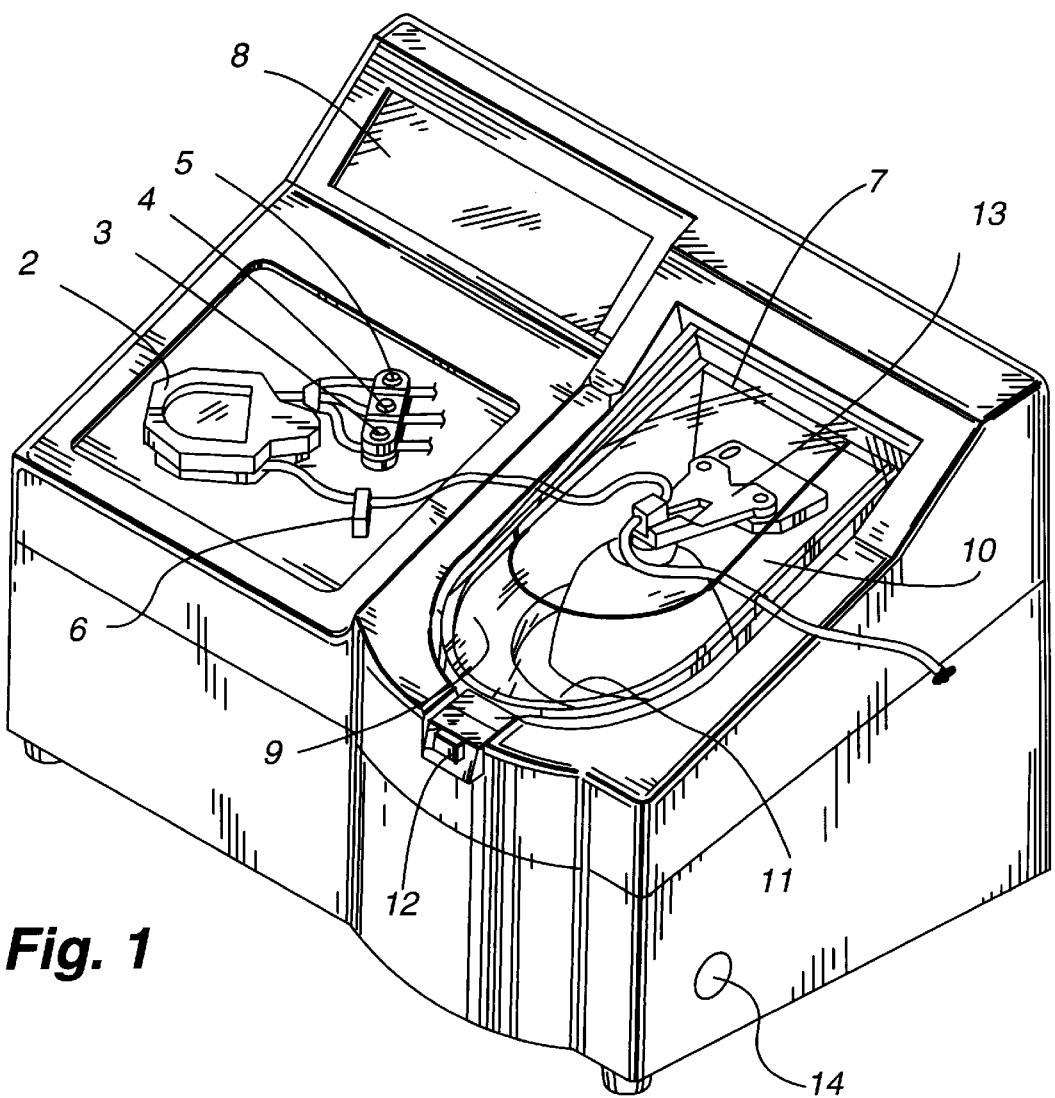
FIG. 1 is a perspective view of a blood separation system embodying the present invention.

Referring now to FIG. 1 there is shown a blood separation system embodying features of the present invention including a housing 1, a peristaltic pump 2, first, second, third clamps 3, 4, 5, an air bubble sensor 6, a centrifuge 7, and a touch sensitive control screen 8. The housing 1 is in general hexahedral or block shaped with vertical front wall, back wall, right side wall and left side wall, horizontal bottom wall, and top wall sloping downward from back to front.

The centrifuge 7 includes a centrifuge housing 9, a centrifuge cover 10, centrifuge drive means 11, a centrifuge latch 12, an upper centrifuge bowl clamp 13 and a drain port 14. The centrifuge 7 is mounted within the right half of housing 1 and is vibrationally isolated from housing 1. The top edge of centrifuge housing 10 slopes downwardly and forwardly so that the top edge is planar with the top surface of housing 1 when centrifuge 7 is installed in housing 1. Centrifuge cover 10 is a shatter resistant transparent dome, convex up, pivotally attached to the back of centrifuge housing 9, shaped so that the lower edge of centrifuge cover 10 covers the exterior of the top edge of centrifuge housing 9 forming a baffle and seals centrifuge 7 when centrifuge cover 10 is closed. Centrifuge latch 12 is attached to the front of centrifuge housing 9 and centrifuge cover 10, and retains centrifuge cover 10 in a closed position whenever centrifuge 7 is operating.

Centrifuge drive means 11 is mounted in the bottom of centrifuge housing 9 and is variable speed, rotating between about 1000 rpm and 6000 rpm in 100 rpm increments. Upper centrifuge bowl clamp 13 is rigidly attached to the back wall of centrifuge housing 9. Drain port 14 exits the centrifuge housing 9 at the lower right side, extending to the right side of housing 1, providing drainage of washing/cleaning liquid during maintenance and drainage of blood component if the centrifuge bowl breaks.

Pump 2 is rigidly attached to left, forward portion of the top of housing 1 with the inlet and outlet of pump 2 generally directed away from the front, left corner of the top of housing 1. Pump 2 is reversible and variable speed with capacity to pump between about 10 ml/min. and 1000 ml/min.

First, second, third clamps 3, 4, 5 are rigidly attached to the top of housing 1 adjacent to the inlet to pump 2. Clamps 3, 4, 5 are color coded, first clamp 3 blue, second clamp 4 yellow and third clamp 5 red. Air bubble sensor 6 is rigidly attached to the top of housing 1 adjacent to the outlet to pump 2.

Touch sensitive control screen 8 is mounted in housing 1 at the rear, left portion of the top of housing 1, facing toward the front of housing 1.

Figure 2:
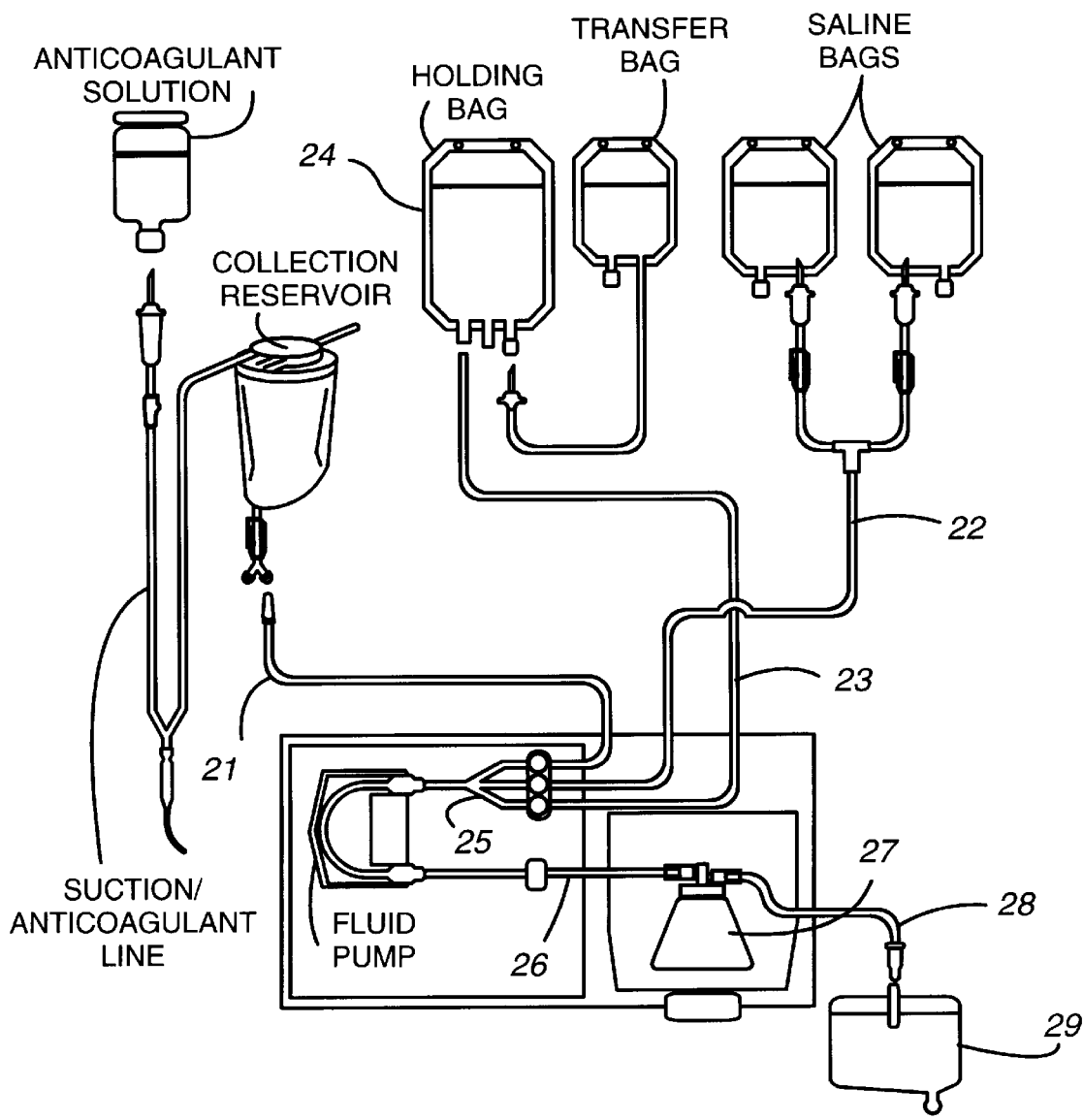
FIG. 2 is a diagram showing the sterile, disposable components of a blood separation system embodying the present invention.

Referring to FIG. 2, a blood processing kit includes the disposable components of the blood separation system, including blood source tubing 21, saline wash tubing 22, processed blood tubing 23, processed blood holding bag 24, a first 4-way connector 25, pump header tubing 26, a centrifuge bowl 27, centrifuge exit tubing 28 and waste bag 29. Blood source tubing 21 is color coded blue, connecting to the source of the blood to be processed at a first end, passing through third clamp 5, and connecting to the first 4-way connector 25 at the second end. Saline wash tubing 22 is color coded yellow, connecting to a saline source at a first end, passing through second clamp 4, and connecting to the first 4-way connector 25 at the second end. Processed blood tubing 23 is color coded red, connecting to processed blood holding bag 24 at a first end, passing through first clamp 3, and connecting to the first 4-way connector 25 at the second end. Pump tubing header connects to first 4-way connector at a first end, passes through pump 2, air bubble sensor 6 and the left edge of centrifuge cover 10, and connects to centrifuge bowl 27 at the second end.

Centrifuge bowl 27 is installed in centrifuge 7, the base of centrifuge bowl 27 being held and rotated by centrifuge drive means 11 and the top of centrifuge bowl 27 being stabilized by upper centrifuge bowl clamp 13. Centrifuge exit tubing 28 connects to centrifuge bowl 27 at a first end, passes through the right edge of centrifuge cover 10, and connects at a second end to waste bag 29 which hang on the right side of housing 1.

Figure 3:
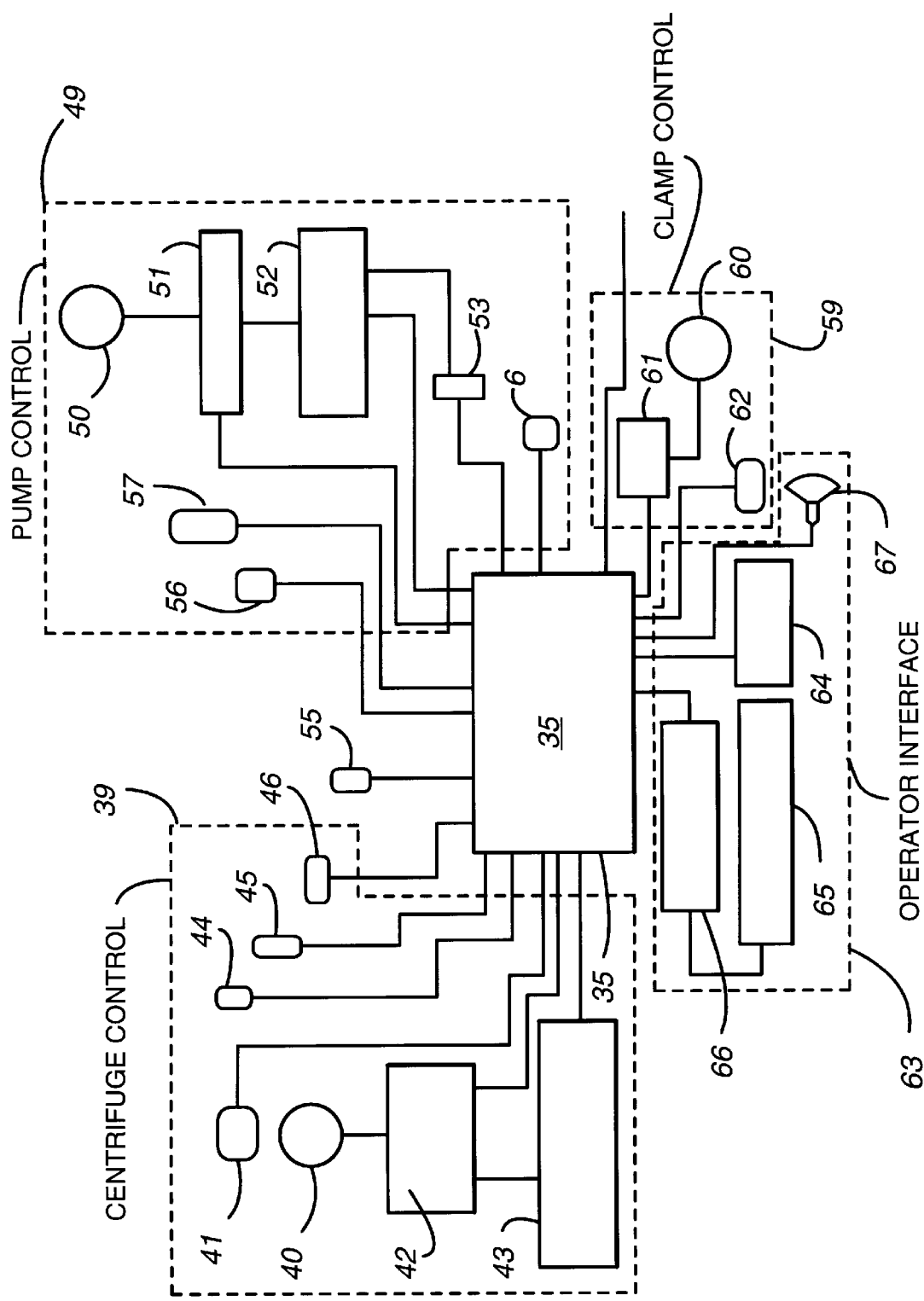
FIG. 3 is control system diagram of a blood separation system embodying the present invention.

FIG. 3 shows the control system for a blood separation system embodying the present invention. The control system includes centrifuge control 39, pump control 49, clamp control 59, operator interface 63 and system controller that is central processing unit 35.

Centrifuge control 39 has a centrifuge motor 40 that rotates the centrifuge drive means 11, a centrifuge motor controller 43 and centrifuge brake controller 42 that control the speed of rotation of centrifuge motor 40, a centrifuge hall sensor 41 and a centrifuge encoder 44 that independently monitor the speed of rotation of centrifuge motor 40, a centrifuge cover sensor 46 that senses whether centrifuge cover 10 is closed, and a centrifuge cover lock 45 that locks centrifuge latch 12 whenever centrifuge motor 40 is rotating above about 60 rpm.

Pump control 49 includes pump motor 50 that drives pump 2, pump relay 51 that supplies power to pump motor 50, pump motor controller 52 that controls the speed and direction of pump motor 50, pump hall sensor 57 and pump encoder 56 that independently monitor the speed and direction of rotation of pump motor 50, pump lid sensor 53 that senses whether the pump cover is closed, air bubble sensor 6 that senses whether fluid or air is flowing through pump header 26, and level sensor 55 which signals when centrifuge bowl 27 is full of red cells.

Clamp control 59 includes clamp motor 60 which opens and closes first, second and third clamps 3, 4, 5, clamp motor controller 61 which controls clamp motor 60, and clamp position sensor 62 that determines the position of first, second and third clamps 3, 4, 5.

The operator interface 63 includes a speaker 67 and the touch sensitive control screen 8 which has a display 64, touch screen 65 and touch screen controller 66. Touch screen 65 is transparent, physically mounts over the display 64, and provides operator input to the blood separation system. Display 64 is a 40 character by 6 line green fluorescent screen, and provides output and operator instructions. FIG. 4 shows examples of screen displays. Speaker 67 sounds an alarm signal when an alarm condition occurs in the blood separation system.

Central processing unit 35 coordinates the operation of the blood separation system, operating the pump 2, clamps 3, 4, 5, and centrifuge 7 in the proper sequence, direction and speeds, preventing pump 2 operation if the pump cover is open, preventing centrifuge 7 operation if the centrifuge cover 10 is open, locking centrifuge latch 12 when centrifuge 7 is rotating above about 60 rpm, monitoring fluid flow through air bubble sensor 6, and displaying system status, pump volume and centrifuge speed during operation. Referring to FIGS. 4C and 4D, central processing unit 35 also provides a series of tutorial screens that guide the operator, step by step, through the setup of the disposable components of a blood processing kit, and screens showing the details of each alarm condition when such alarm condition occurs. Referring to FIG. 4A and 4B, after an operator selects an operation on touchscreen 65, central processing unit 35 requires the operator to "accept" the selection by touching the ACCEPT position on touchscreen 65 before the blood separation system will proceed.

Central processing unit 35 has six preprogrammed software programs in ROM (Read Only Memory) including a Standard Program, Program A/trauma type applications, Program B/orthopedic applications, Program C/small volume applications, Program D/salvage type applications, and CONPLT/Concentrated Platelet Rich Plasma Sequestration. Programs A, B, C, D and CONPLT may be permanently reprogrammed by the operator, changes being stored in non-volatile RAM (Random Access Memory) maintained by battery back-up. The Standard Program and Programs A, B, C, D, CONPLT may be temporarily changed, the changes being lost when the blood separation system is turned off.

The Standard Program and Programs A, B, C, D may be run in "Automatic" mode. When "Automatic" mode is selected the blood separation system will proceed through the following steps without operator input. The first cycle is the fill cycle which starts with closing first clamp 3 and second clamp 4, and opening third clamp 5. The centrifuge drive means 11 begins to rotate, spinning centrifuge bowl 27. When centrifuge 7 reaches about 5100 rpm pump 2 starts to pump unprocessed blood into centrifuge bowl 27. As the centrifuge bowl 27 fills with blood, the heavier red cells are forced to the outside of centrifuge bowl 27 by centrifugal force while the lighter, undesirable components of the blood are forced inward, up and out of centrifuge bowl 27 through centrifuge exit tubing 28 to waste bag 29. When level sensor 55 detects that centrifuge bowl 27 is full of red cells the fill cycle ends.

The wash cycle starts with third clamp 5 closing, second clamp 4 opening and pump 2 beginning to pump saline wash into centrifuge bowl 27. After a predetermined period of time the wash cycle terminates, and pump 2 and centrifuge 7 stop. The empty cycle begins and pump 2 begins to pump fluid out of centrifuge bowl 27. A small predetermined volume of fluid is backflushed into saline tubing 22, then second clamp 4 closes and first clamp 3 opens so that the remaining washed red cells are pumped through the processed blood tubing 23 to holding bag 24 to await transfer to a transfer bag for reinjection into the patient.

The Standard Program and Programs A, B, C, D may also be run in "Semi-Automatic" mode. The blood separation system in "Semi-Automatic" mode follows the above sequence of steps but enters a standby mode at the end of the fill cycle and the end of the wash cycle, requiring operator selection of the next cycle before proceeding.

Figure 5:
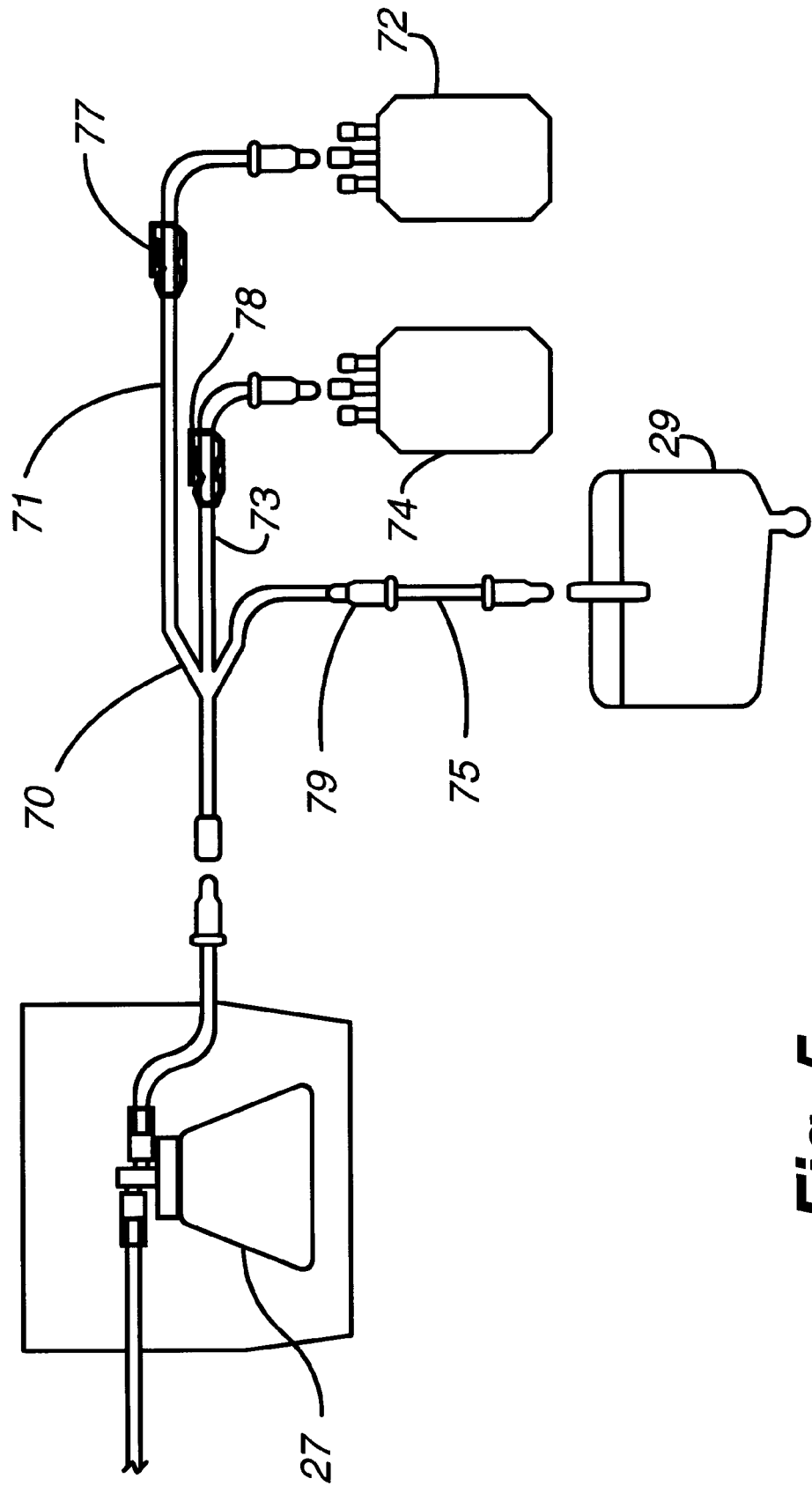
FIG. 5 is a diagram showing the sterile, disposable components for platelet rich plasma sequestration for a blood separation system embodying the present invention.
Figure 6A:
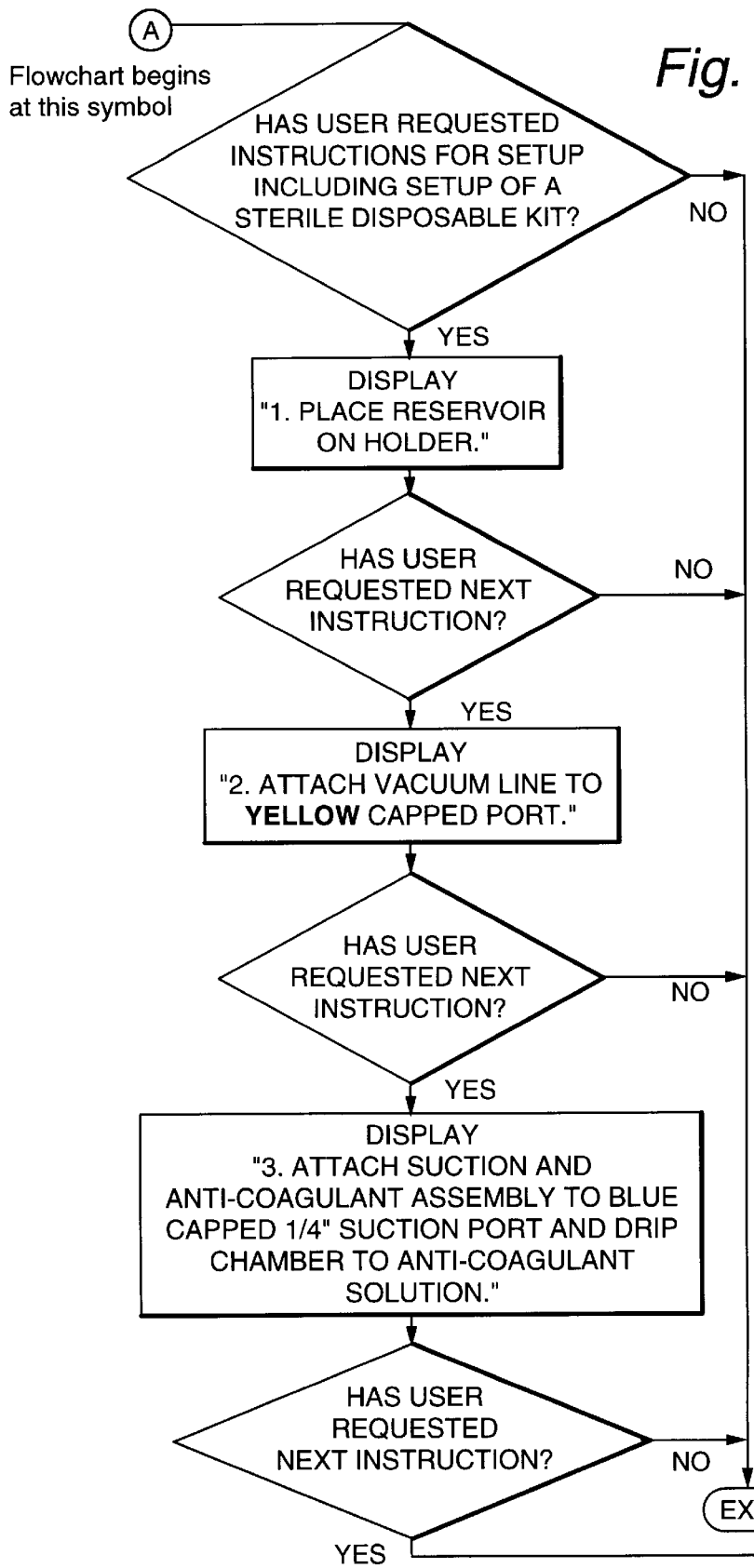
FIGS. 6A, 6B, 6C, 6D, 6E, 6F, 6G, 6H, 6I, 6J, 6L and 6M are flow charts of a software program for a central processing unit for a blood separation system embodying the present invention.
Figure 6B:
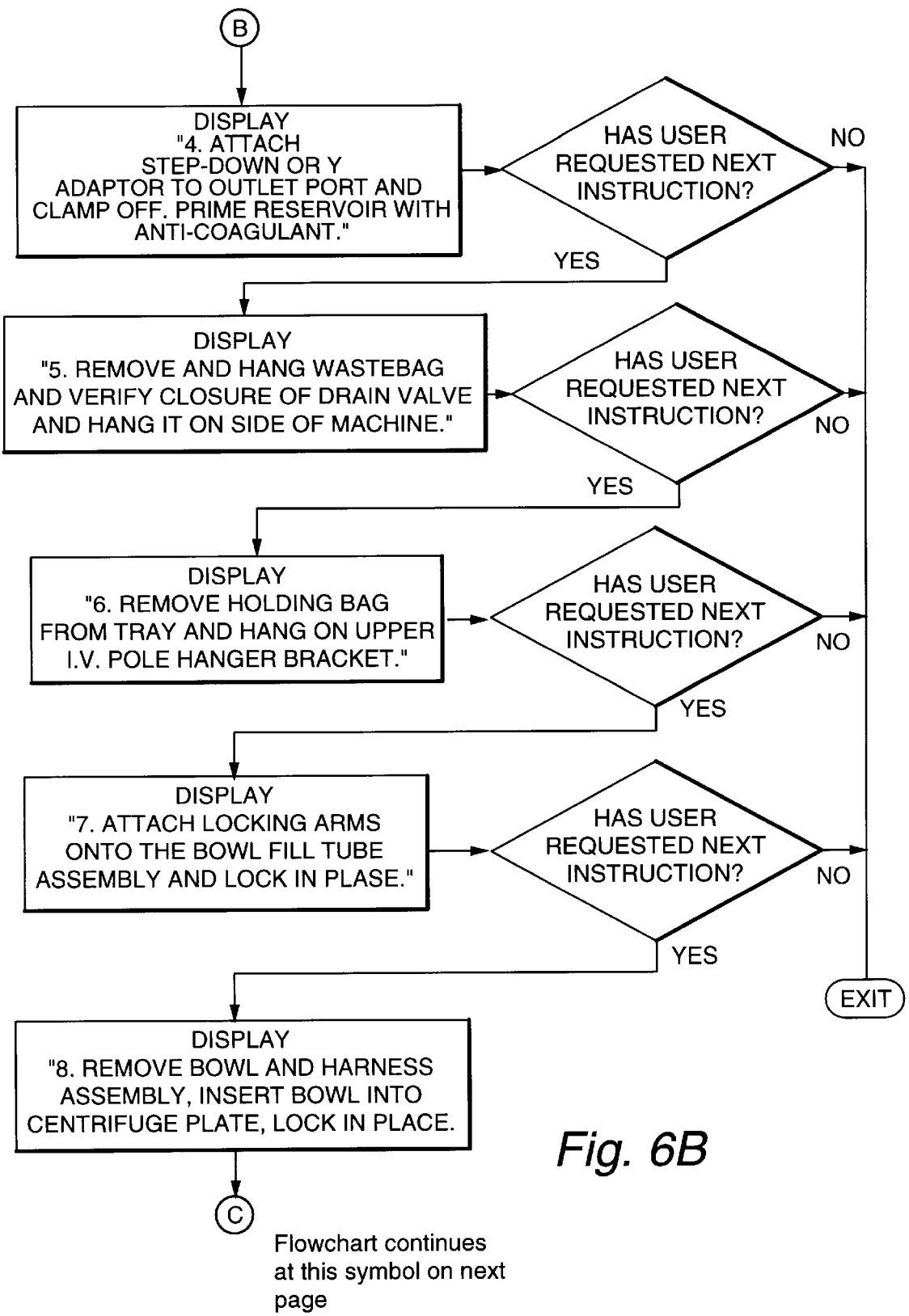
Figure 6C:
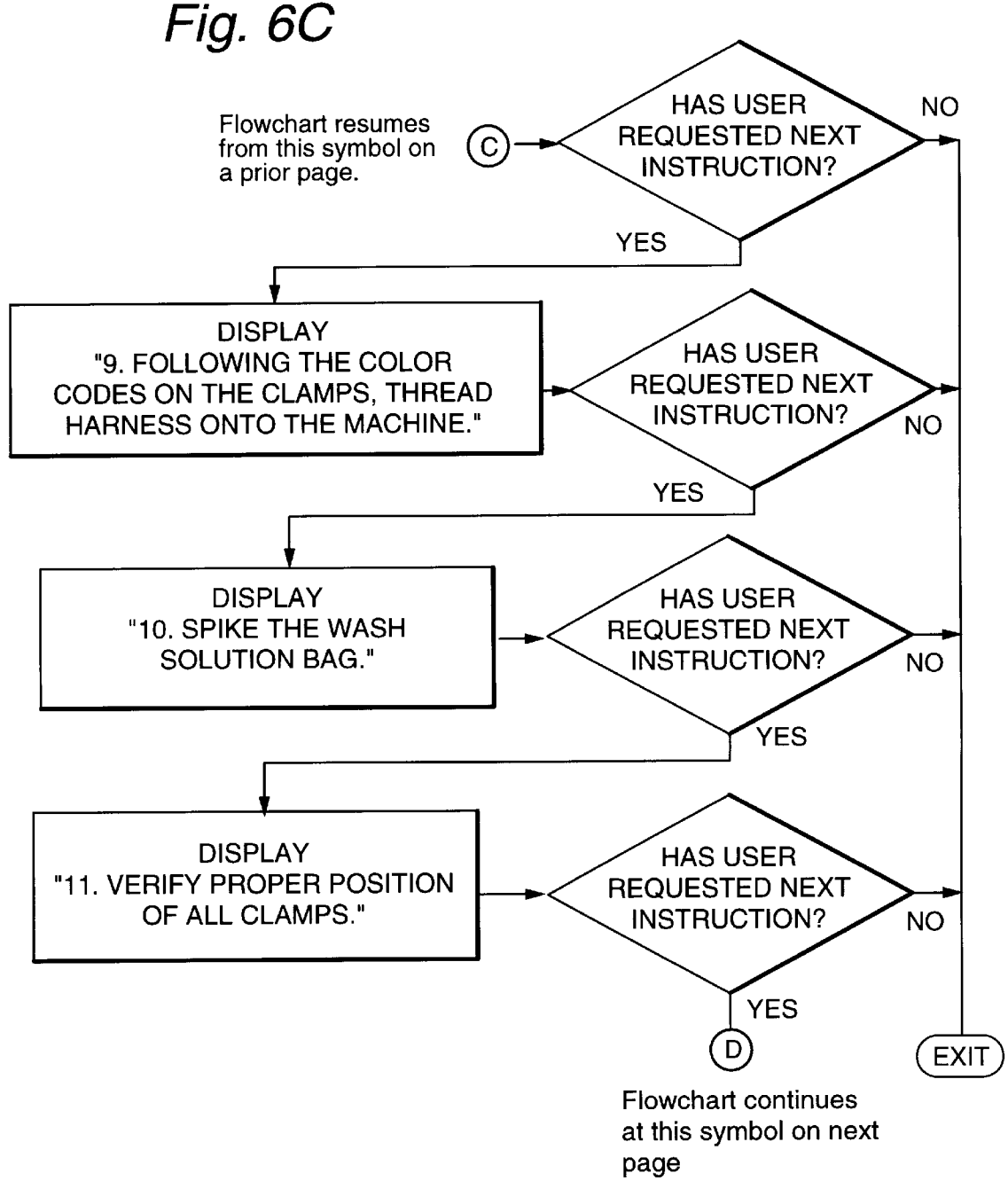
Figure 6E:
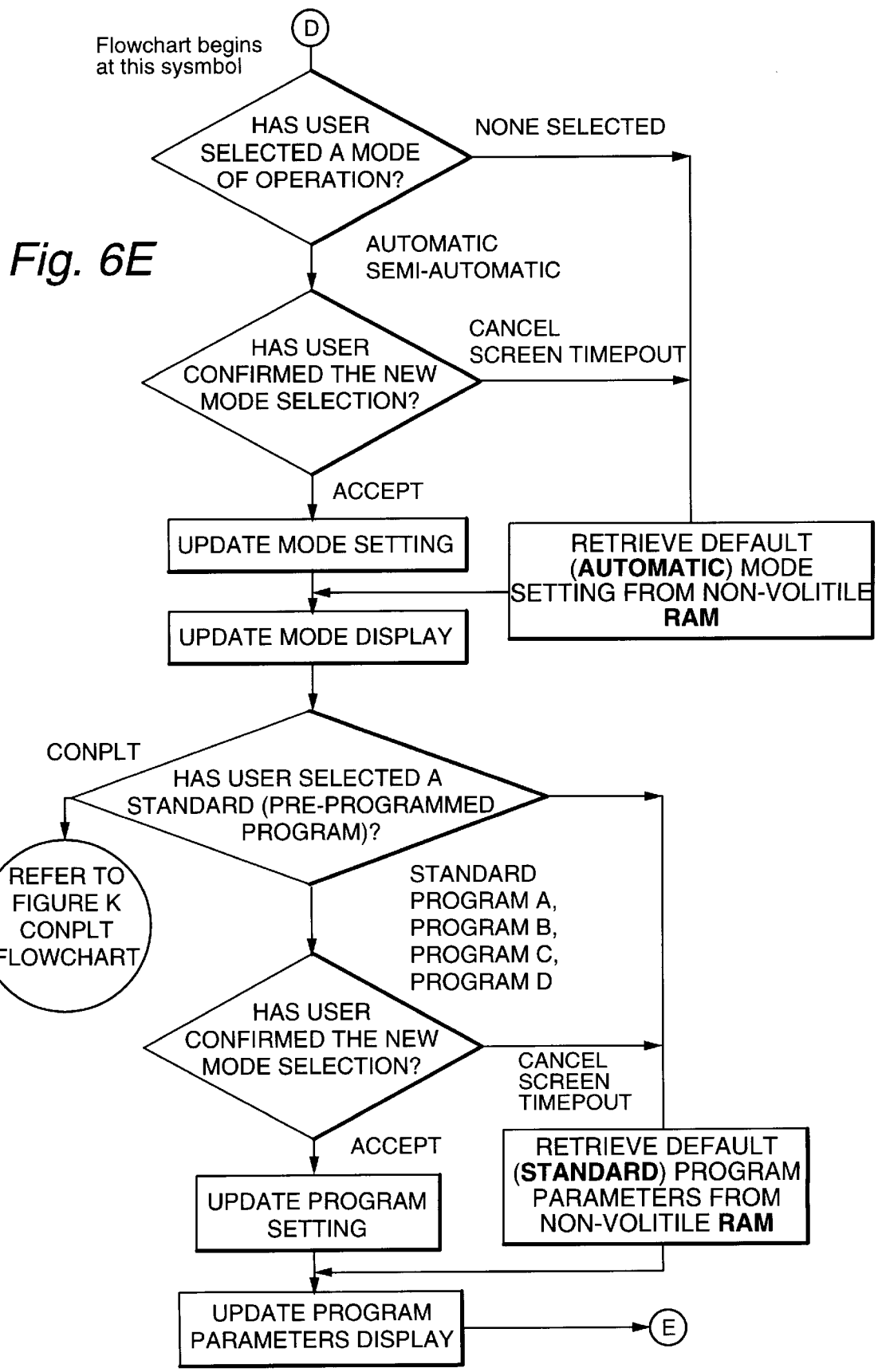
Figure 6F:
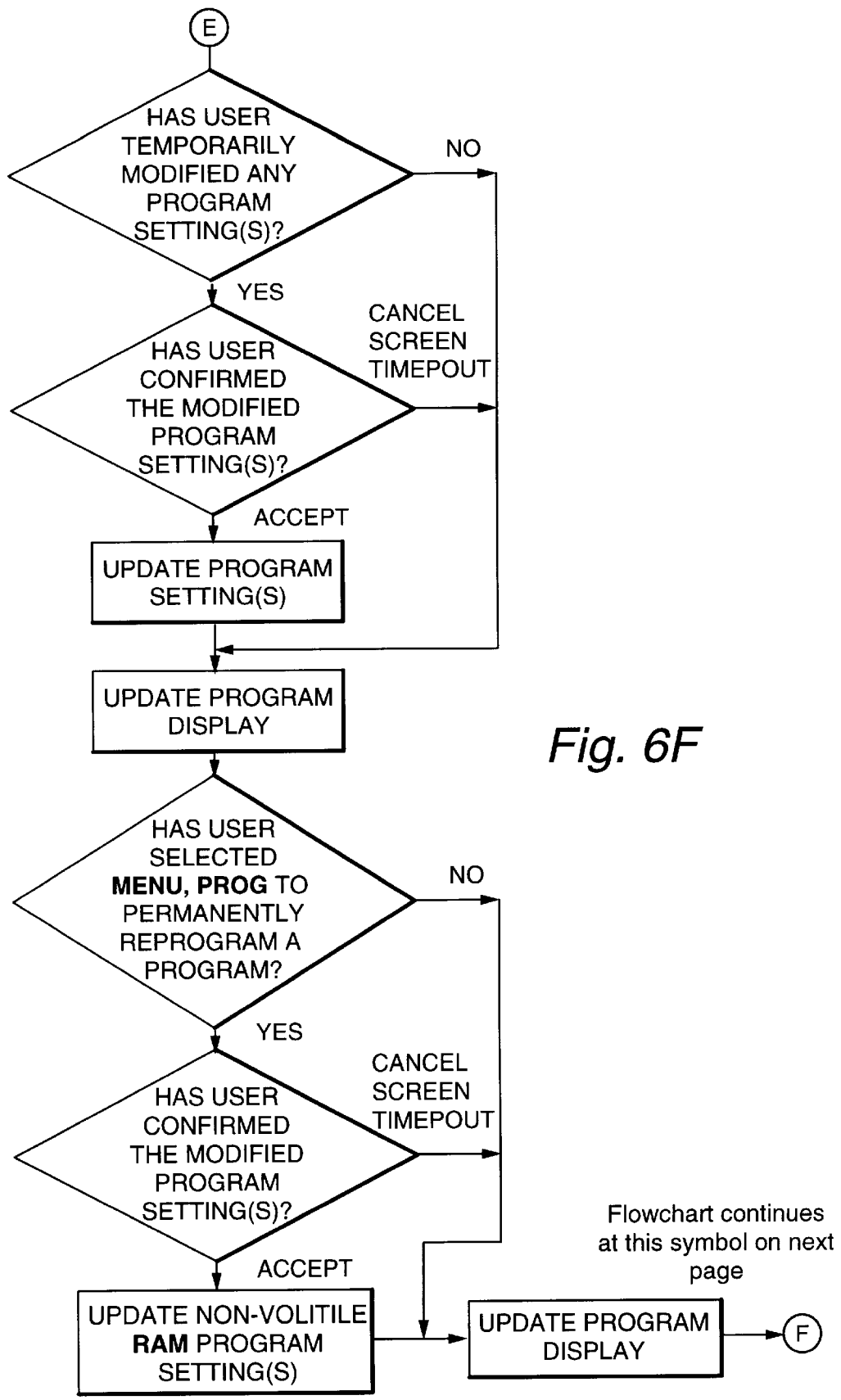
Figure 6G:
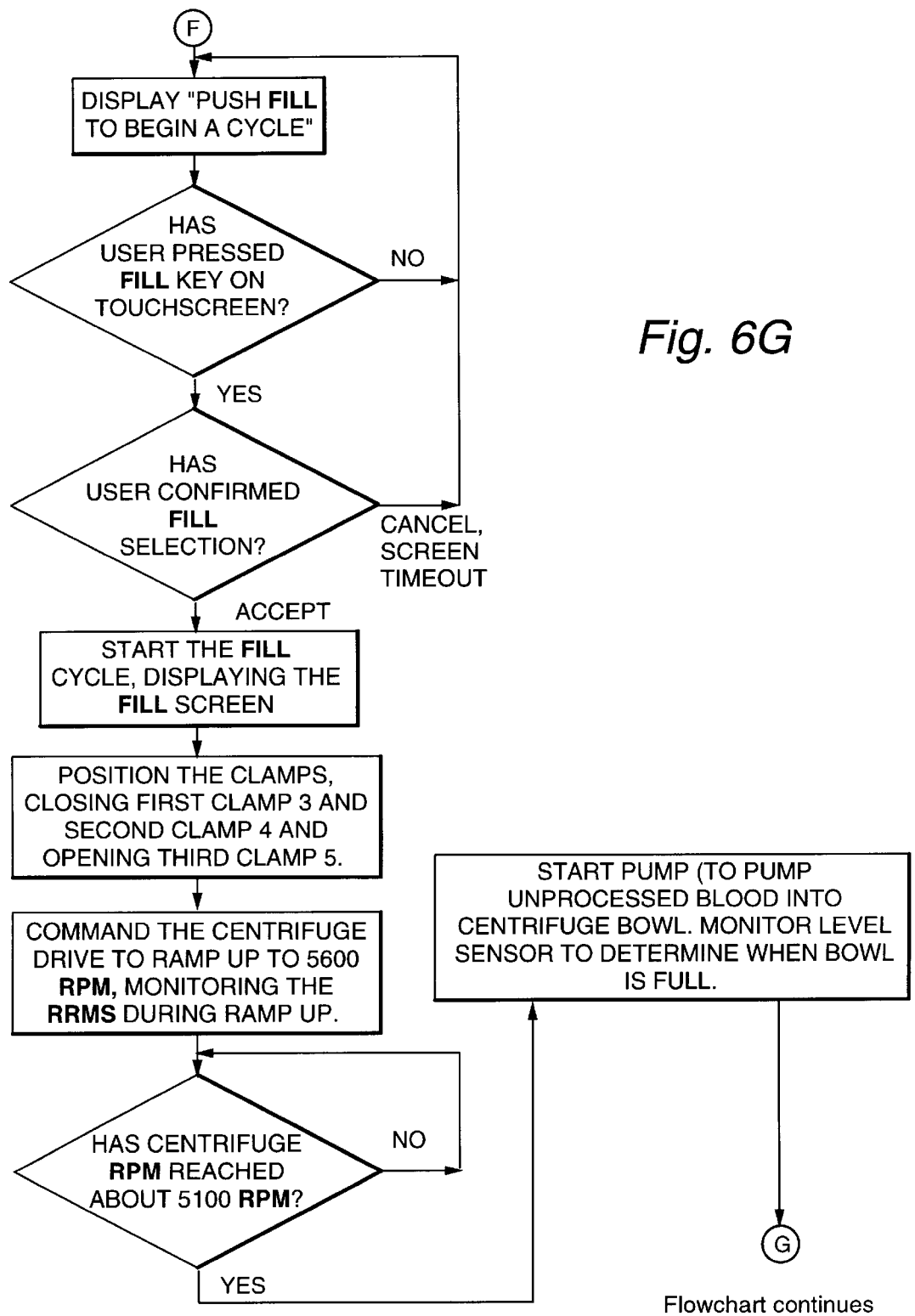
Figure 6H:
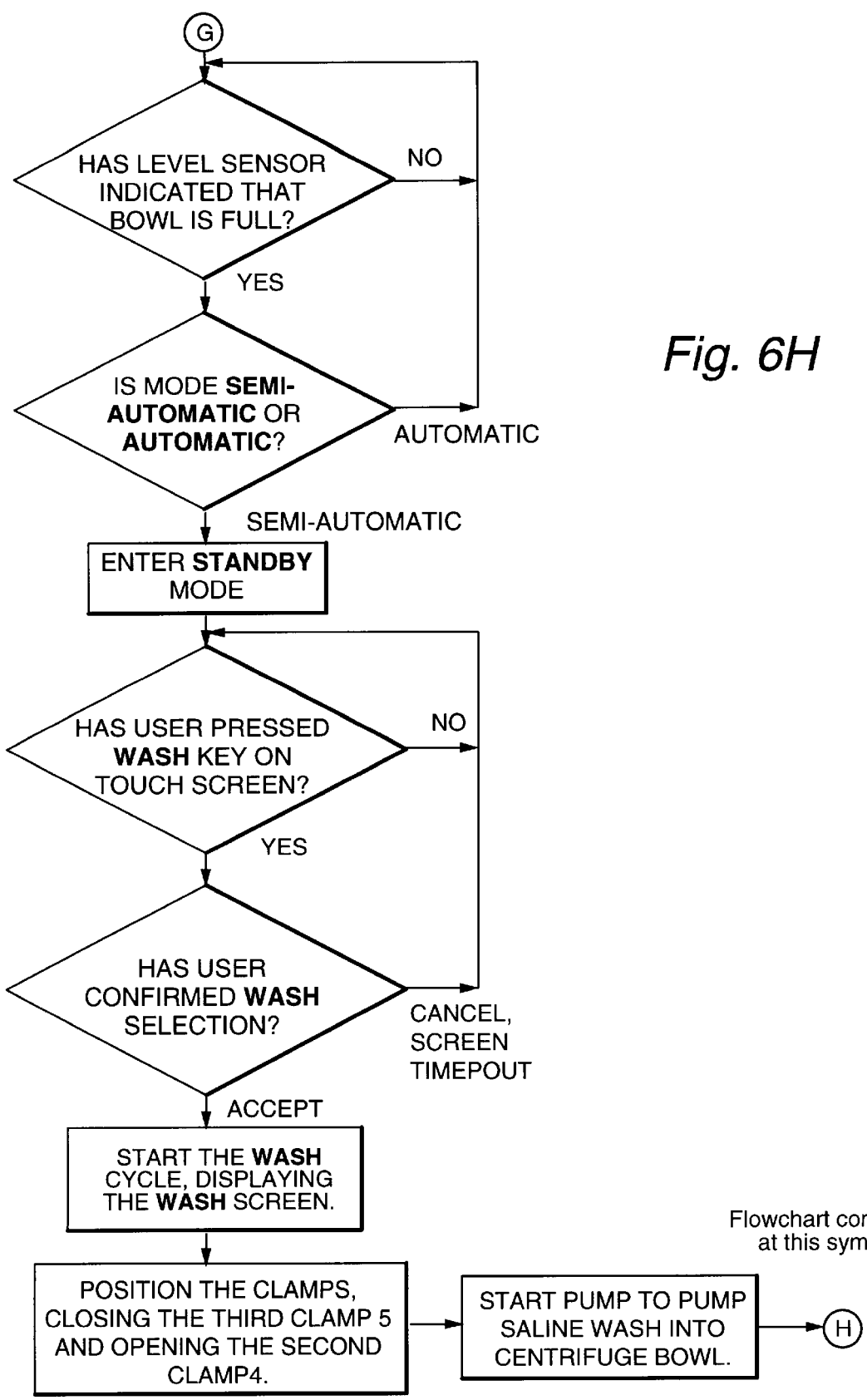
Figure 6I:
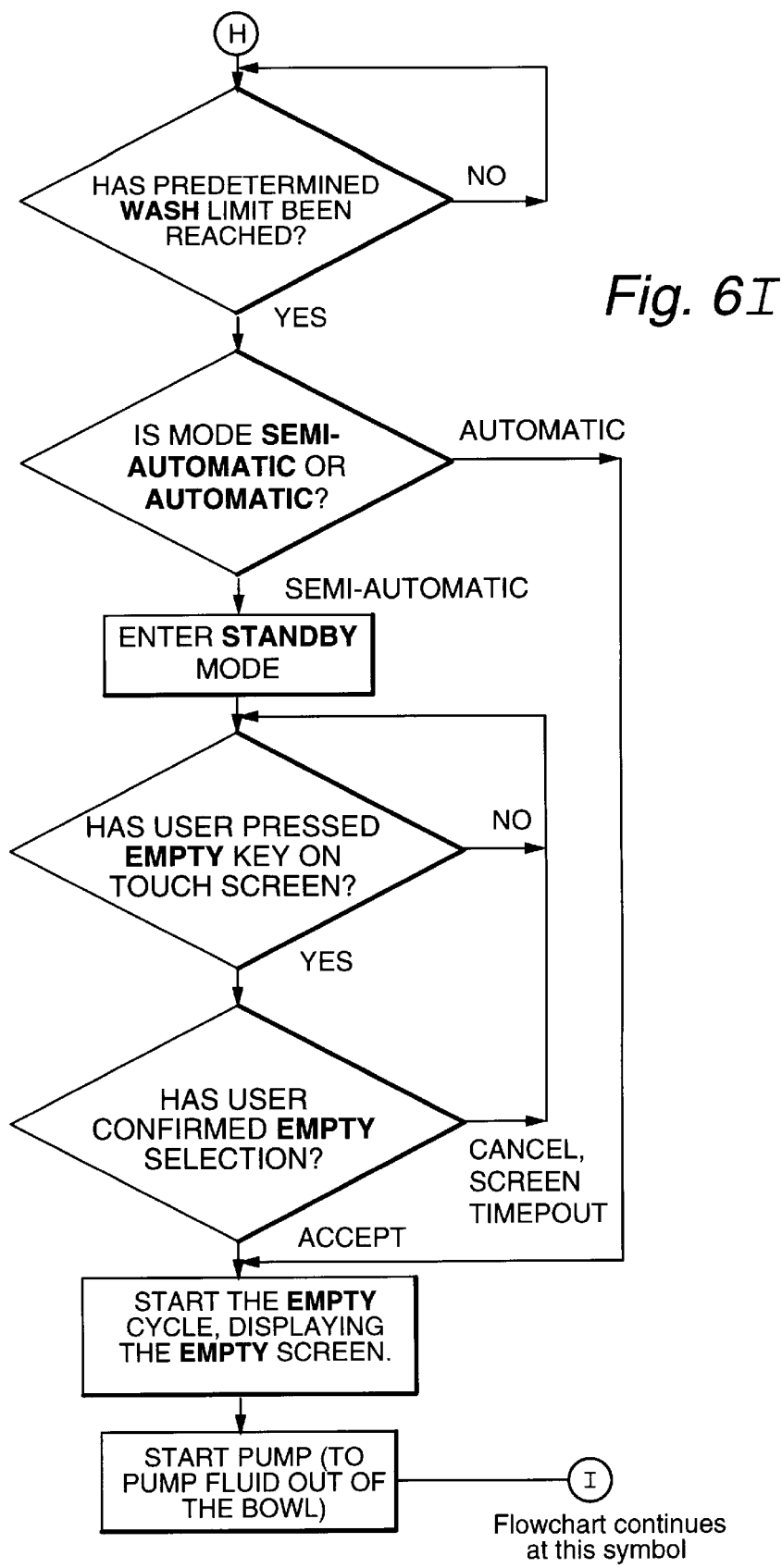
Figure 6J:
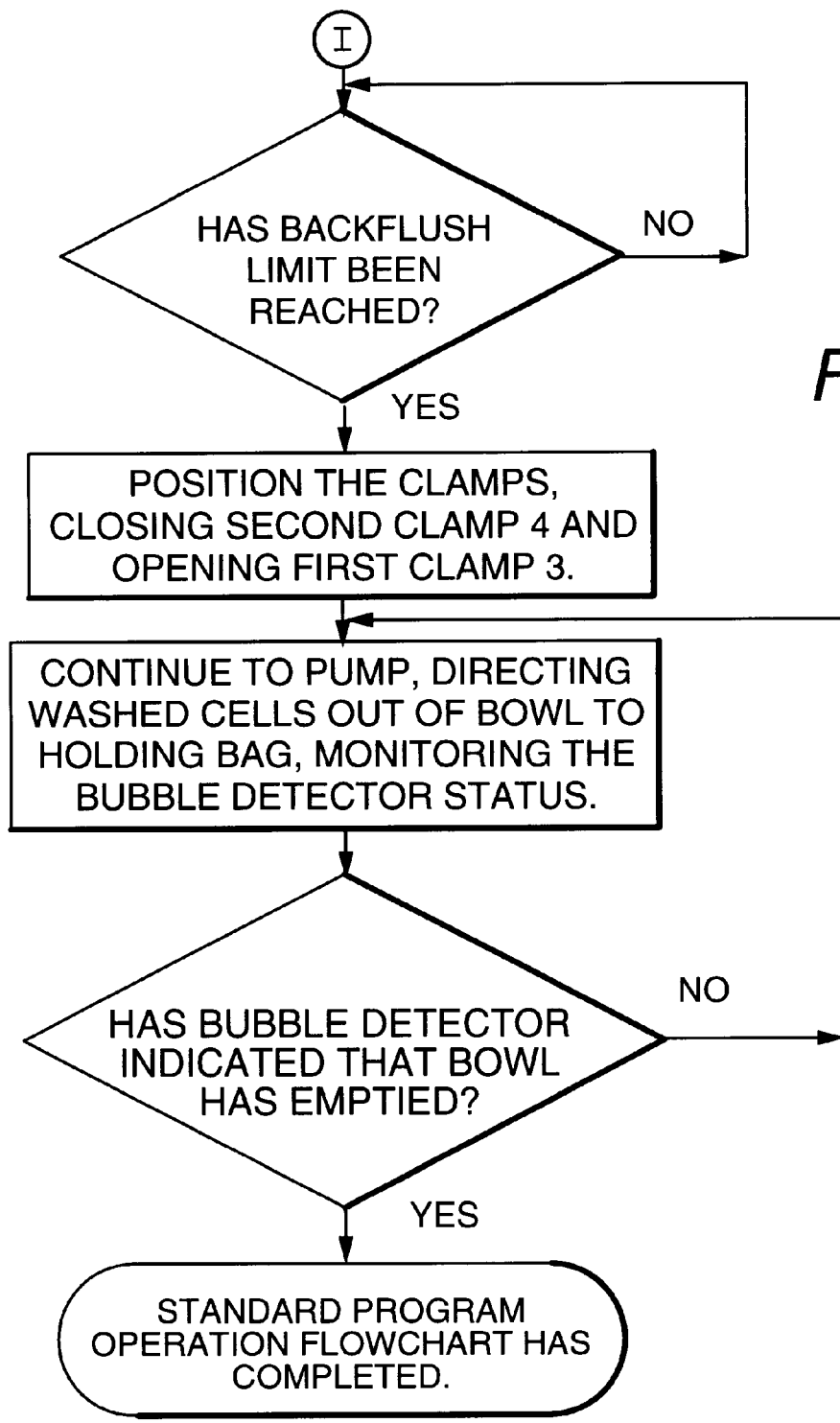
Figure 6K:
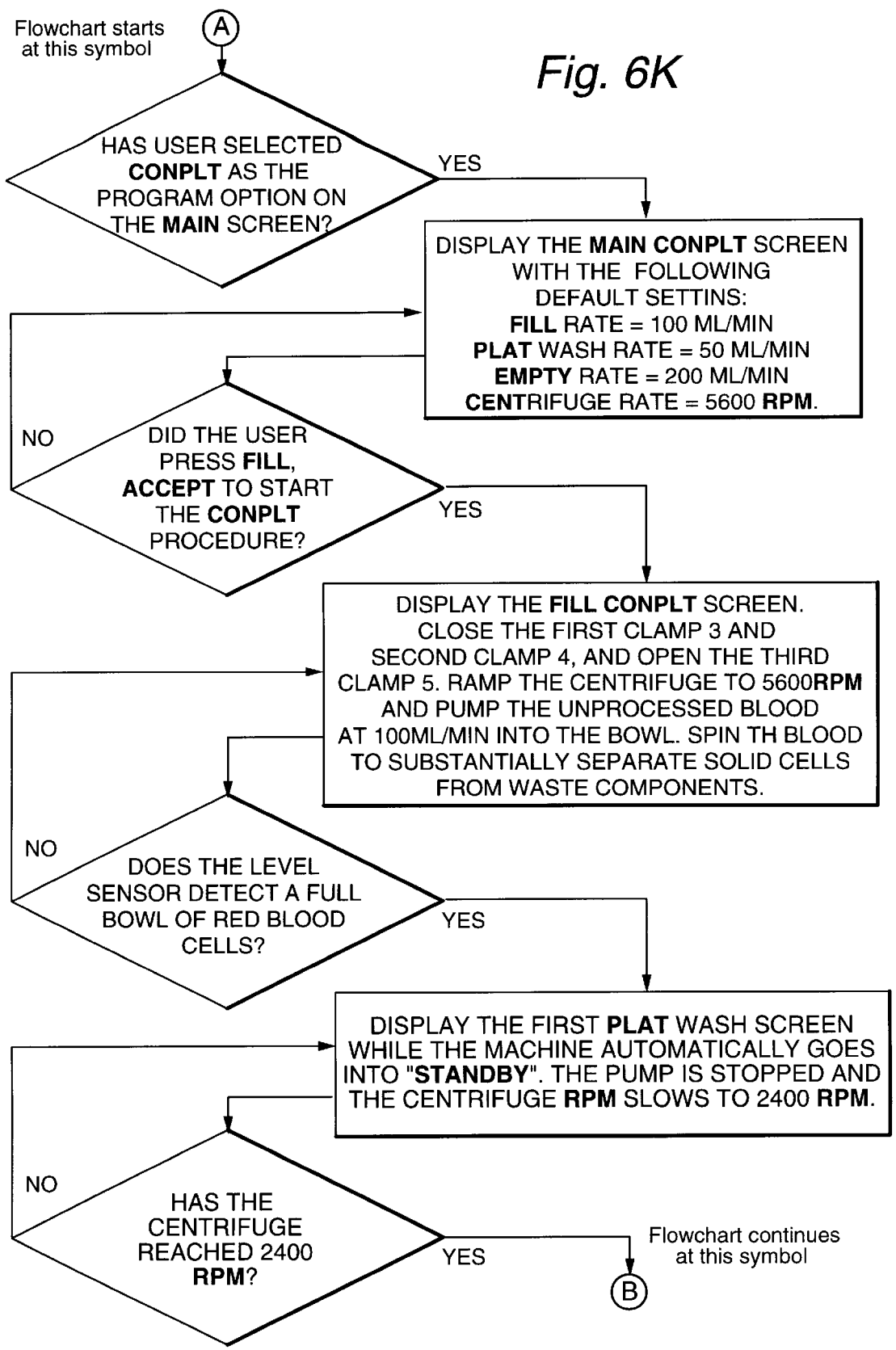
Figure 6L:
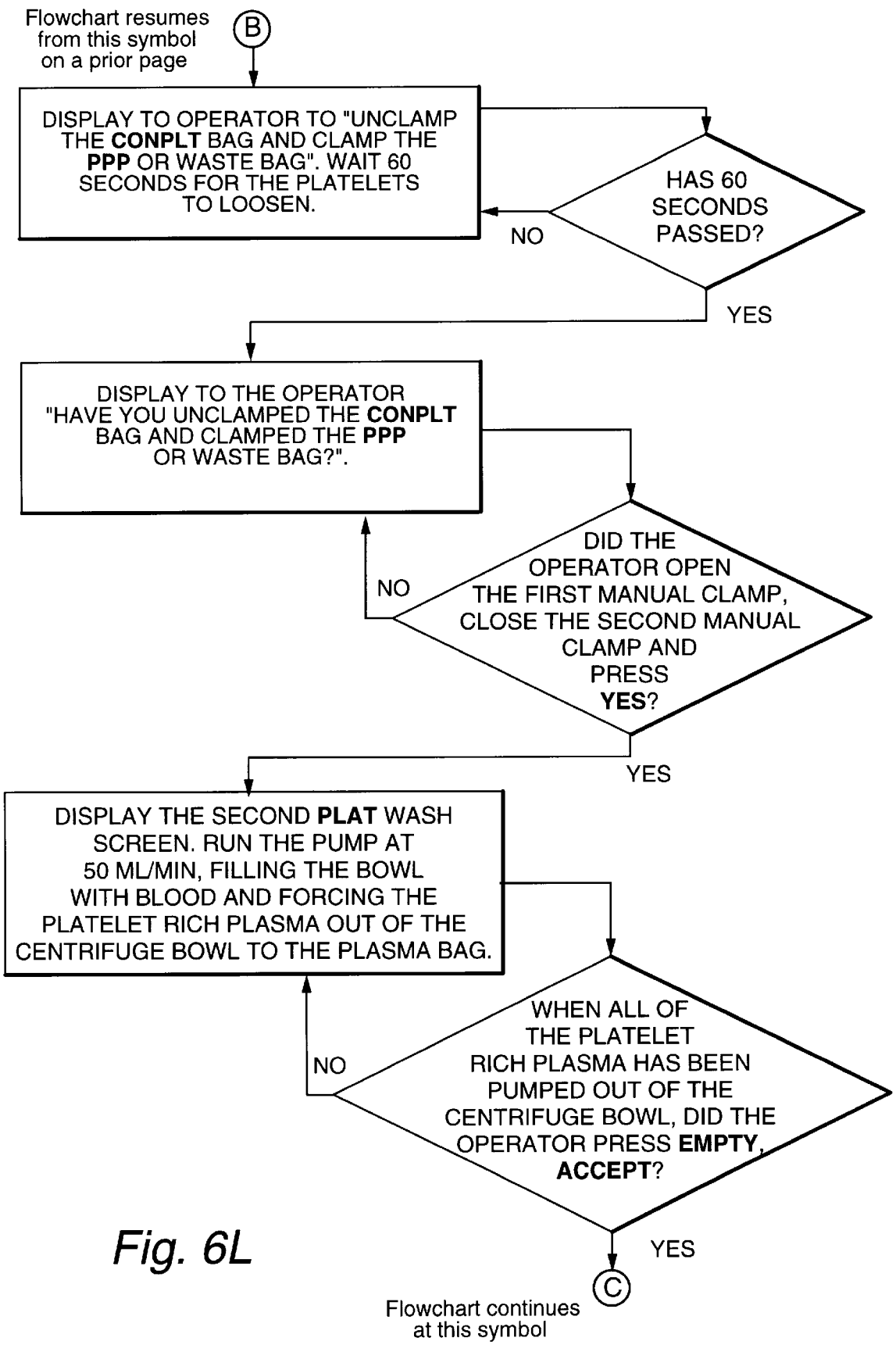
Figure 6M:
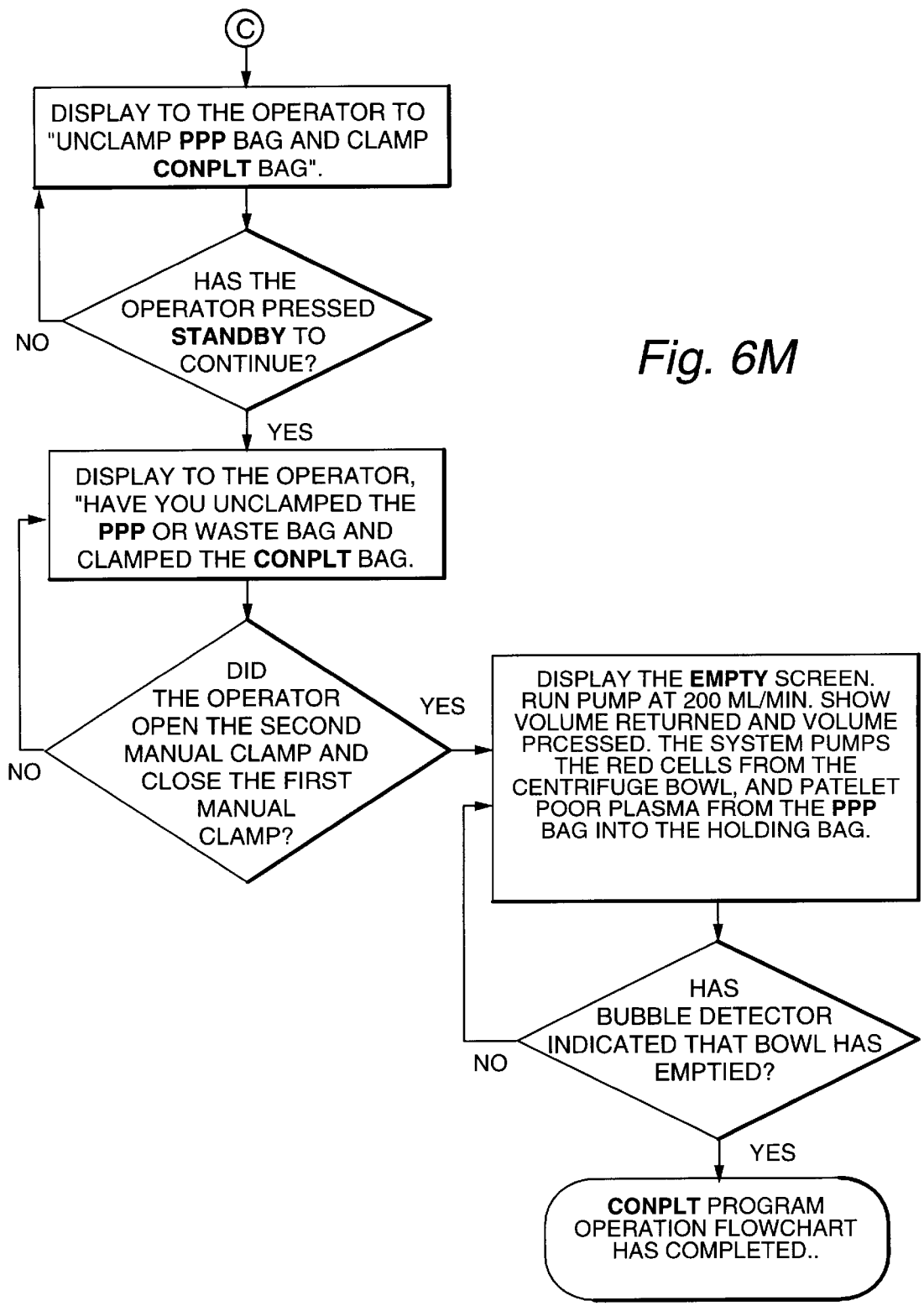

The blood separation system embodying features of the present invention will efficiently provide platelet rich plasma sequestration with the CONPLT Program. Referring to FIG. 5, the setup of the disposable components for platelet rich plasma sequestration is similar to the setup for red cell separation and washing but further includes a second 4-way connector 70, platelet rich plasma tubing 71 connecting to second 4-way connector 70 at a first end, connecting to a platelet rich plasma (PRP) bag 72 at a second end and having a first manual clamp 77 in the middle which is closed during setup, platelet poor plasma tubing 73 connecting to second 4-way connector 70 at a first end, connecting to a platelet poor plasma (PPP) bag 74 at a second end and having a second manual clamp 78 in the middle which is closed during setup, and waste tubing 75 connecting to second 4-way connector 70 at a first end, connecting to waste bag 29 at a second end and having a third manual clamp 79 in the middle which is opened during setup. For platelet rich plasma sequestration the second end of centrifuge exit tubing 28 connects to 4-way connector 70 instead connecting to the waste bag 29 as in the standard setup.

Platelet rich plasma sequestration begins with a fill cycle identical to the fill cycle described above for the standard blood processing procedure. The fill cycle starts with closing first clamp 3 and second clamp 4, and opening third clamp 5. The centrifuge drive means 11 begins to rotate, spinning centrifuge bowl 27. When centrifuge 7 reaches about 5100 rpm pump 2 starts to pump unprocessed blood into centrifuge bowl 27. As the centrifuge bowl 27 fills with blood, the heavier red cells are forced to the outside of centrifuge bowl 27 by centrifugal force while the lighter, undesirable components of the blood are forced inward, up and out of centrifuge bowl 27 through centrifuge exit tubing 28 to waste bag 29. If conservation of platelet poor plasma is desired, when the effluent reaches the first end of centrifuge exit tubing 28, the operator places the blood separation system in "STANDBY" mode, opens second manual clamp 73, closes third manual clamp 79 and releases "STANDBY" mode. When level sensor 55 detects that centrifuge bowl 27 is full of red cells the fill cycle ends.

At the end of the fill cycle the autotranfusion system automatically goes into "STANDBY" mode, slows the centrifuge 7 speed to about 2400 rpm, and displays the messages "Wait 60 seconds to loosen platelets" and "Unclamp PRP bag, then clamp PPP bag" on display 64. The operator will manually open first manual clamp 77 and close second manual clamp 78. After 60 seconds the platelet rich plasma separates from the red cells and moves to the inside top of centrifuge bowl 27. The autotranfusion system displays the message "Have you unclamped the PRP bag and clamped the PPP bag?" on display 64. When the operator confirms opening first manual clamp 77 and closing second manual clamp 78, the autotranfusion system will again begin pumping blood into centrifuge bowl 27, forcing the platelet rich plasma out of centrifuge bowl 27, through centrifuge exit tubing 28, second 4-way connector 70 and platelet rich plasma tubing 71, to platelet rich plasma bag 72.

When all of the platelet rich plasma has been pumped out of centrifuge bowl 27 and centrifuge exit tubing 28 begins to fill with red cells, the operator presses "EMPTY" then "ACCEPT" on touchscreen 65. The blood separation system will display the message "Unclamp PPP bag and clamp PRP bag" and "Press STANDBY to continue" on display 64. After the operator presses "STANDBY", the blood separation system will display the message "Have you unclamped PPP bag and clamp PRP bag?" on display 64. The operator opens second manual clamp 78, closes first manual clamp 77 and presses "YES" on touchscreen 65. The blood separation system pumps the red cells from the centrifuge bowl 27 and platelet poor plasma from platelet poor plasma bag 74 into holding bag 24, completing the platelet rich plasma sequestration.

Although the present invention has been described with a certain degree of particularity, it is understood that the present disclosure has been made by way of example and that changes in details of structure may be made without departing from the spirit thereof.

What is claimed is:

1. A blood separation system comprising:
   a blood separator for separating blood into blood components,
   a plurality of collectors coupled to said blood separator for receiving said blood components,
   a controller for said blood separator,
   an output device coupled to said controller for displaying text messages, said output device displaying a plurality of instructions that guide an operator to perform predetermined operations, and
   an input device coupled to said controller for allowing an operator to input commands to said controller,
   said controller requiring confirmation of each command by said operator prior to executing each command.

2. A blood separation system as set forth in claim 1 wherein said output device displays detailed instructions for setup including setup of a sterile, disposable kit that includes all elements that physically contact said blood components.

3. A blood separation system as set forth in claim 1 further comprising:
   a blood separator control coupled to said controller for controlling the operation of said blood separator,
   a pump connected to said blood separator for pumping said blood and said blood components to and from said blood separator,
   a pump control coupled to said controller for controlling said pump,
   a plurality of clamps connected to said pump and to said collectors and to a source of blood for controlling the flow of said blood and said blood components to and from said pump,
   a clamp control coupled to said controller for controlling said clamp.

4. A blood separation system as set forth in claim 3 wherein said controller is a programmable central processing unit,
   said blood separator is a centrifuge, said blood separator control includes a centrifuge motor that rotates said centrifuge, a centrifuge motor controller and a centrifuge brake controller that control the speed of rotation of said centrifuge motor, a centrifuge hall sensor and a centrifuge encoder that independently monitor the speed of rotation of said centrifuge motor, a centrifuge cover sensor that senses whether a centrifuge cover is closed, and a centrifuge cover lock that locks a centrifuge latch whenever said centrifuge rotates above a predetermined speed, said pump control includes a pump motor that drives said pump, a pump relay that supplies power to said pump motor, a pump motor controller that controls the speed and direction of said pump motor, a pump hall sensor and a pump encoder that independently monitor the speed and direction of rotation of said pump motor, a pump lid sensor that senses whether a pump cover is closed, an air bubble sensor that senses whether fluid or air is flowing through said pump header, and a level sensor which signals when said centrifuge is full, and said clamp control includes a clamp motor which opens and closes said clamps, a clamp motor controller that controls said clamp motor, and a clamp position sensor that determines the position of said clamps.

5. A blood separation system as set forth in claim 1 further comprising:

a 4-way connector, a first tube connected between a source of blood and said connector for transporting said blood from said source to said connector, a first clamp located on an intermediate portion of said first tube for occluding flow through said first tube, a source of saline for washing said blood, a second tube connected between said source of saline and said connector for transporting said saline from said source to said connector, a second clamp located on an intermediate portion of said second tube for occluding flow through said second tube, a third tube connected between said connector and one of said collectors for transporting reusable blood components from said connector to said collector, a third clamp located on an intermediate portion of said third tube for occluding flow through said third tube, a fourth tube connected between said connector and said blood separator for transporting fluids between said connector and said blood separator, said blood separator being a centrifuge, a peristaltic pump located along an intermediate portion of said fourth tube for pumping fluids through said fourth tube, a fifth tube coupled to said blood separator for transporting waste blood components from said centrifuge, and a waste bag for collecting said waste blood components, said controller operating said pump and said clamps to control transport of fluids through said tubes, and said centrifuge.

6. A blood separation system as set forth in claim 1 further comprising a blood separator control coupled to said controller for controlling the operation of said blood separator.

7. A blood separation system as set forth in claim 6 wherein said blood separator is a centrifuge, and said blood separator control includes a centrifuge motor that rotates said centrifuge, a centrifuge motor controller and a centrifuge brake controller that control the speed of rotation of said centrifuge motor, a centrifuge hall sensor and a centrifuge encoder that independently monitor the speed of rotation of said centrifuge motor, a centrifuge cover sensor that senses whether a centrifuge cover is closed, and a centrifuge cover lock that locks a centrifuge latch whenever said centrifuge rotates above a predetermined speed.

8. A blood separation system as set forth in claim 1 further comprising:

a pump connected to said blood separator for pumping said blood and said blood components to and from said blood separator, and a pump control coupled to said controller for controlling said pump.

9. A blood separation system as set forth in claim 8 wherein said pump control includes a pump motor that drives said pump, a pump relay that supplies power to said pump motor, a pump motor controller that controls the speed and direction of said pump motor, a pump hall sensor and a pump encoder that independently monitor the speed and direction of rotation of said pump motor, a pump lid sensor that senses whether a pump cover is closed, an air bubble sensor that senses whether fluid or air is flowing through said pump header, and a level sensor which signals when said centrifuge is full.

10. A blood separation system as set forth in claim 1 further comprising:

a plurality of clamps connected to said pump and to said collectors and to a source of blood for controlling the flow of said blood and said blood components to and from said pump, and a clamp control coupled to said controller for controlling said clamp.

11. A blood separation system as set forth in claim 10 wherein said clamp control includes a clamp motor which opens and closes said clamps, a clamp motor controller that controls said clamp motor, and a clamp position sensor that determines the position of said clamps.

12. A blood separation system as set forth in claim 1 wherein said controller is a programmable central processing unit.

13. A blood separation system for sequestration of platelet rich plasma comprising:

a centrifugal blood separator, a waste bag coupled to said blood separator for collecting waste blood components with a first clamp that occludes flow between said waste bag and said blood separator, at least one collection bag coupled to said blood separator for collection of said platelet rich plasma with a second clamp that occludes flow between said collection bag and said blood separator a controller for said blood separator, an output device coupled to said controller for displaying text messages, said output device displaying instructions that instruct an operator to open and close said clamps, and an input device coupled to said controller for allowing an operator to input commands to said controller, said controller requiring confirmation of each instruction by said operator prior to executing each instruction.

14. An autotransfusion system comprising:

a first device for supplying blood from a patient, a blood separator coupled to said first device for separating waste products from usable blood components, a second device coupled to said blood separator for collecting said usable blood components for reinjection into said patient, a control system coupled to said blood separator for controlling said first device, said second device and said blood separator so that each step that an operator command said control system to perform must be confirmed to prevent accidental commands from being performed by said control system.

15. A blood separation system comprising:

a blood separator for separating blood into blood components, a plurality of collectors coupled to said blood separator for receiving said blood components, a controller for said blood separator, an output device coupled to said controller for displaying text messages, said output device displaying a plurality of instructions that guide an operator to perform predetermined operations, and an input device coupled to said controller for allowing an operator to input commands to said controller, said controller requiring confirmation by the operator that each instruction was performed prior to continuing through said plurality of instructions.

16. A blood separation system as set forth in claim 15 wherein said output device displays detailed instructions for setup including setup of a sterile, disposable kit that includes all elements that physically contact said blood components.

17. A blood separation system as set forth in claim 15 further comprising:

a blood separator control coupled to said controller for controlling the operation of said blood separator, a pump connected to said blood separator for pumping said blood and said blood components to and from said blood separator, a pump control coupled to said controller for controlling said pump, a plurality of clamps connected to said pump and to said collectors and to a source of blood for controlling the flow of said blood and said blood components to and from said pump, a clamp control coupled to said controller for controlling said clamp.

18. A blood separation system as set forth in claim 17 wherein said controller is a programmable central processing unit, said blood separator is a centrifuge, said blood separator control includes a centrifuge motor that rotates said centrifuge, a centrifuge motor controller and a centrifuge brake controller that control the speed of rotation of said centrifuge motor, a centrifuge hall sensor and a centrifuge encoder that independently monitor the speed of rotation of said centrifuge motor, a centrifuge cover sensor that senses whether a centrifuge cover is closed, and a centrifuge cover lock that locks a centrifuge latch whenever said centrifuge rotates above a predetermined speed, said pump control includes a pump motor that drives said pump, a pump relay that supplies power to said pump motor, a pump motor controller that controls the speed and direction of said pump motor, a pump hall sensor and a pump encoder that independently monitor the speed and direction of rotation of said pump motor, a pump lid sensor that senses whether a pump cover is closed, an air bubble sensor that senses whether fluid or air is flowing through said pump header, and a level sensor which signals when said centrifuge is full.

said clamp control includes a clamp motor which opens and closes said clamps, a clamp motor controller that controls said clamp motor, and a clamp position sensor that determines the position of said clamps.

19. A blood separation system as set forth in claim 15 further comprising:

a 4-way connector, a first tube connected between a source of blood and said connector for transporting said blood from said source to said connector, a first clamp located on an intermediate portion of said first tube for occluding flow through said first tube, a source of saline for washing said blood, a second tube connected between said source of saline and said connector for transporting said saline from said source to said connector, a second clamp located on an intermediate portion of said second tube for occluding flow through said second tube, a third tube connected between said connector and one of said collectors for transporting reusable blood components from said connector to said collector, a third clamp located on an intermediate portion of said third tube for occluding flow through said third tube, a fourth tube connected between said connector and said blood separator for transporting fluids between said connector and said blood separator, said blood separator being a centrifuge, a peristaltic pump located along an intermediate portion of said fourth tube for pumping fluids through said fourth tube, a fifth tube coupled to said blood separator for transporting waste blood components from said centrifuge, and a waste bag for collecting said waste blood components, said controller operating said pump and said clamps to control transport of fluids through said tubes, and said centrifuge.

20. A blood separation system as set forth in claim 15 further comprising a blood separator control coupled to said controller for controlling the operation of said blood separator.

21. A blood separation system as set forth in claim 20 wherein said blood separator is a centrifuge, and said blood separator control includes a centrifuge motor that rotates said centrifuge, a centrifuge motor controller and a centrifuge brake controller that control the speed of rotation of said centrifuge motor, a centrifuge hall sensor and a centrifuge encoder that independently monitor the speed of rotation of said centrifuge motor, a centrifuge cover sensor that senses whether a centrifuge cover is closed, and a centrifuge cover lock that locks a centrifuge latch whenever said centrifuge rotates above a predetermined speed.

22. A blood separation system as set forth in claim 15 further comprising:

a pump connected to said blood separator for pumping said blood and said blood components to and from said blood separator, and a pump control coupled to said controller for controlling said pump.

23. A blood separation system as set forth in claim 22 wherein said pump control includes a pump motor that drives said pump, a pump relay that supplies power to said pump motor, a pump motor controller that controls the speed and direction of said pump motor, a pump hall sensor and a pump encoder that independently monitor the speed and direction of rotation of said pump motor, a pump lid sensor that senses whether a pump cover is closed, an air bubble sensor that senses whether fluid or air is flowing through said pump header, and a level sensor which signals when said centrifuge is full.

24. A blood separation system as set forth in claim 15 further comprising:
   a plurality of clamps connected to said pump and to said collectors and to a source of blood for controlling the flow of said blood and said blood components to and from said pump, and
   a clamp control coupled to said controller for controlling said clamp.

25. A blood separation system as set forth in claim 24 wherein said clamp control includes a clamp motor which opens and closes said clamps, a clamp motor controller that controls said clamp motor, and a clamp position sensor that determines the position of said clamps.

26. A blood separation system as set forth in claim 15 wherein said controller is a programmable central processing unit.

27. A blood separation system for sequestration of platelet rich plasma comprising:
   a centrifugal blood separator,
   a waste bag coupled to said blood separator for collecting waste blood components with a first clamp that occludes flow between said waste bag and said blood separator,
   at least one collection bag coupled to said blood separator for collection of said platelet rich plasma with a second clamp that occludes flow between said collection bag and said blood separator
   a controller for said blood separator,
   an output device coupled to said controller for displaying text messages, said output device displaying instructions that instruct an operator to open and close said clamps,
   an input device coupled to said controller for allowing an operator to input commands to said controller,
   said controller requiring confirmation by the operator that each instruction was performed prior to continuing through said instructions.

28. An autotransfusion system comprising:
   a first device for supplying blood from a patient,
   a blood separator coupled to said first device for separating waste products from usable blood components,
   a second device coupled to said blood separator for collecting said usable blood components for reinjection into said patient,
   a control system coupled to said blood separator for controlling said first device, said second device and said blood separator,
   an output device coupled to said control system for displaying text messages, said output device displaying a plurality of instructions that guide an operator to perform predetermined operations, and
   an input device coupled to said control system for allowing an operator to input commands to said controller,
   said control system requiring confirmation by the operator that each instruction was performed prior to continuing through said instructions.

* * * * *

UNITED STATES PATENT AND TRADEMARK OFFICE
CERTIFICATE OF CORRECTION

PATENT NO. : 5,964,724                                    Page 1 of 1
DATED     : October 12, 1999
INVENTOR(S) : John Rivera, Son Le, Daniel Cheek, Richard Matt and Roger P. Kaminski It is certified that error appears in the above-identified patent and that said Letters Patent is hereby corrected as shown below:

Column 6,
Line 41, "to input commands:" should read -- to input instructions: --
Line 42, "to input command:" should read -- to input instruction: --
Line 42, "executing each command:" should read -- executing each instruction: --

Column 8,
Line 61, "input commands:" should read -- input instructions: --

Column 9,
Line 7, "operator command:" should read -- operator instructs: --
Line 8, "accidental command:" should read -- Accidental instructions: --

Column 12,
Line 9, "input command:" should read -- input instructions: --

Signed and Sealed this

Thirtieth Day of April, 2002

Attest:

Attesting Officer

JAMES E. ROGAN
*Director of the United States Patent and Trademark Office*